United States Patent [19]

Stanton

[11] Patent Number: 4,539,993

[45] Date of Patent: Sep. 10, 1985

[54] FAIL-SAFE MUSCLE STIMULATOR DEVICE
[75] Inventor: David J. Stanton, Anoka, Minn.
[73] Assignee: Medtronic, Inc., Minneapolis, Minn.
[21] Appl. No.: 442,532
[22] Filed: Nov. 18, 1982
[51] Int. Cl.³ .............................................. A61N 1/36
[52] U.S. Cl. .................................................. 128/421
[58] Field of Search ....................... 128/421, 422, 423; 368/8, 9, 10, 93, 107, 108, 112, 262; 371/14; 340/507, 508, 931; 307/441, 442

[56] References Cited

U.S. PATENT DOCUMENTS 3,893,067 7/1975 Watanabe et al. .................. 340/931
4,326,534 4/1982 Axelgaard et al. ................ 128/421

Primary Examiner—William E. Kamm
Attorney, Agent, or Firm—Robert J. Klepinski; Joseph F. Breimayer; John L. Rooney

[57] ABSTRACT

A tissue stimulator of the type which provides short intervals of stimulation followed by longer intervals of rest is provided with a fail-safe system for turning off the stimulator if the stimulation interval exceeds a predetermined maximum interval. A timer times each "on" interval. If the "on" interval exceeds the predetermined maximum, the timer times out and shuts off stimulation.

2 Claims, 5 Drawing Figures

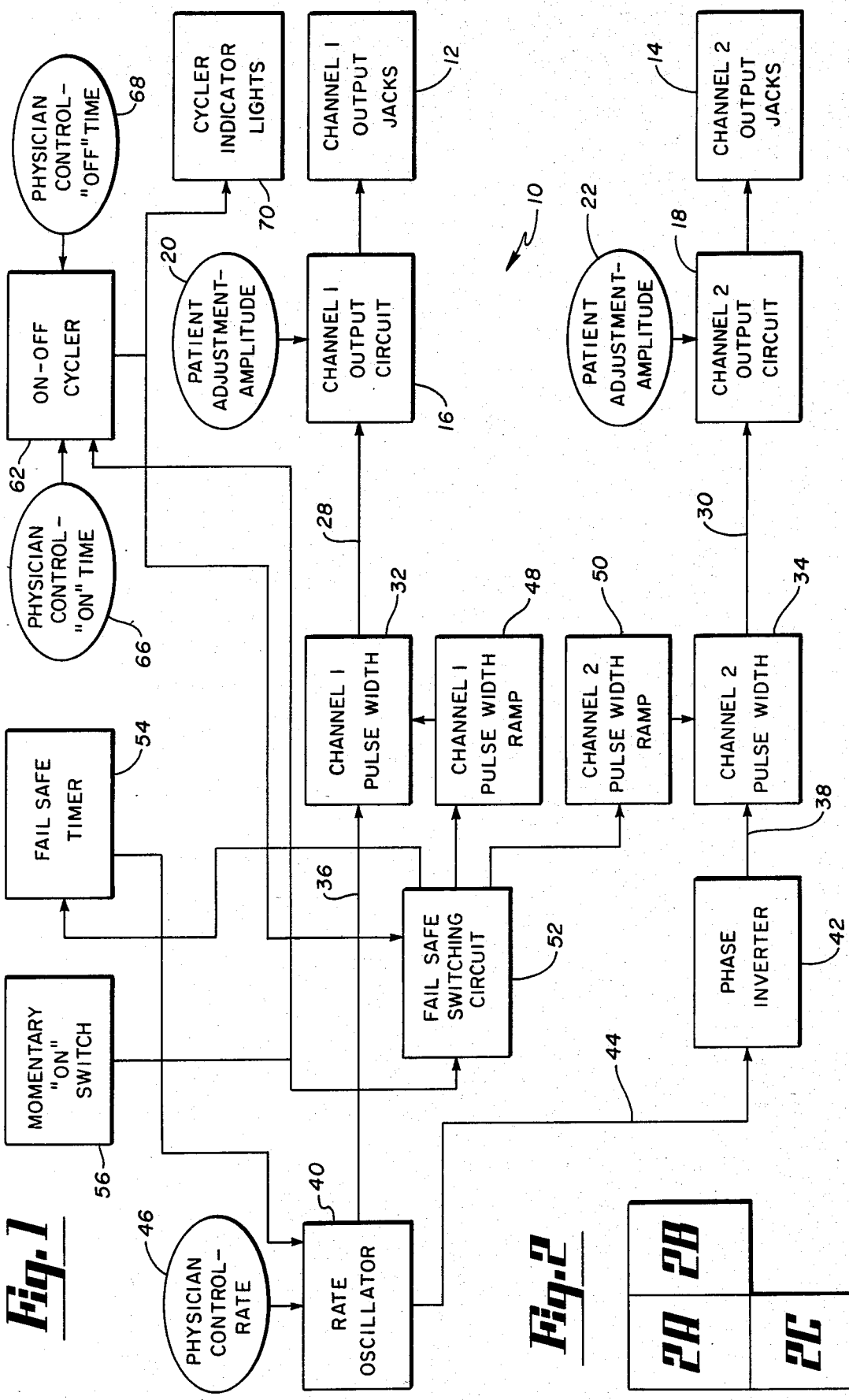

4,539,993

FAIL-SAFE MUSCLE STIMULATOR DEVICE

BACKGROUND OF THE INVENTION

The present invention relates to devices for muscle stimulation, in particular devices which employ safety mechanisms to prevent overstimulation in case of user error or system failure.

It has been found that scoliosis can be treated by electronic muscle stimulating devices. In one class of devices, electrodes are implanted to act upon muscles along the sides of the spine. An RF receiver is implanted to power the electrodes. When treatment is to be administered, an RF transmitter is placed over the receiver to drive the electrodes. For a general discussion of such treatment of scoliosis see "Electrospinal Instrumentation for Scoliosis: Current Status," by Bobeschko, Herbert and Friedman, *Orthopedic Clinics of North America*, Vol. X, No. 4, October, 1979. U.S. Pat. No. 4,026,301 to Friedman et al discloses apparatus and method for treating scoliosis with implanted electrodes. Other devices treat scoliosis transcutaneously through skin-mounted electrodes.

Treatment of scoliosis patients with such a device is usually accomplished during the night while a patient is sleeping. Therefore, the stimulator or transmitter, wires and other external apparatus are not used during the day time hours, which prevents embarrassment to the patient.

If the patient is sleeping during treatment, instantaneous changes in the treatment cannot be immediately recognized by the patient. Normally the treatment consists of short periods of electrical stimulation followed by a longer period of rest. This continues throughout the night. For example, a cycle might contain a five second burst of stimulation followed by a twenty-five second rest period. Should parts of the equipment malfunction, and the duration of the stimulation phase extend too long, irritation to the patient's muscles may result. If, for example, constant stimulation occurred, the patient would eventually wake up, but soreness of the back might result.

While failures of such circuitry have not been clinically observed, in a product where a patient's health is concerned it is imperative to take all possible precautions in preventing possible equipment failures from irritating the patient.

Some such stimulation devices include a constant stimulation button, which can be activated by the patient to obtain a steady stream of stimulation. To ensure that such a constant stimulation button is not misused, or that the user does not activate it for an improperly extended period, it is desirable that the stimulator be designed to deactivate before the constant stimulation can have undesirable medical effects.

An example of a previous muscle stimulator which may be used in the treatment of scoliosis is disclosed in U.S. Pat. No. 4,392,496 by David J. Stanton, issued July 12, 1983. Part of the circuitry disclosed in this application is disclosed and claimed in that application.

SUMMARY OF THE INVENTION

The present invention relates to a fail-safe system including a fail-safe switch means and fail-safe timer means, for use in a tissue stimulator of a type which includes means for allowing a periodic signal with a cycler means for repetitively allowing the signal for a predetermined on-time interval and inhibiting the signal for predetermined off-time interval. Stimulation is provided to the patient during the on-time interval. The off-time interval constitutes a rest period. In a stimulator constructed according to the present invention the fail-safe timer means times the duration of the on-time interval. Time-out means in the timer means shuts off the timer means when a maximum time interval is reached before termination of the on-time interval. Reset means resets the timer means, preferably at the beginning of each "on" interval, so that the timer means is able to begin timing the subsequent "on" time interval.

The maximum "on" time interval is preferably 40 seconds.

The muscle stimulator preferably includes a user-actuated "on" switch means for turning on power to the stimulator and means for resetting the timer means when the "on" switch means is actuated.

BRIEF DESCRIPTION OF THE DRAWINGS

FIG. 1 is a functional block diagram of a dual channel neuromuscular stimulator system including a fail-safe switching circuit and fail-safe timer constructed according to the present invention.

DETAILED DESCRIPTION OF THE PREFERRED EMBODIMENT

Figure 2A:
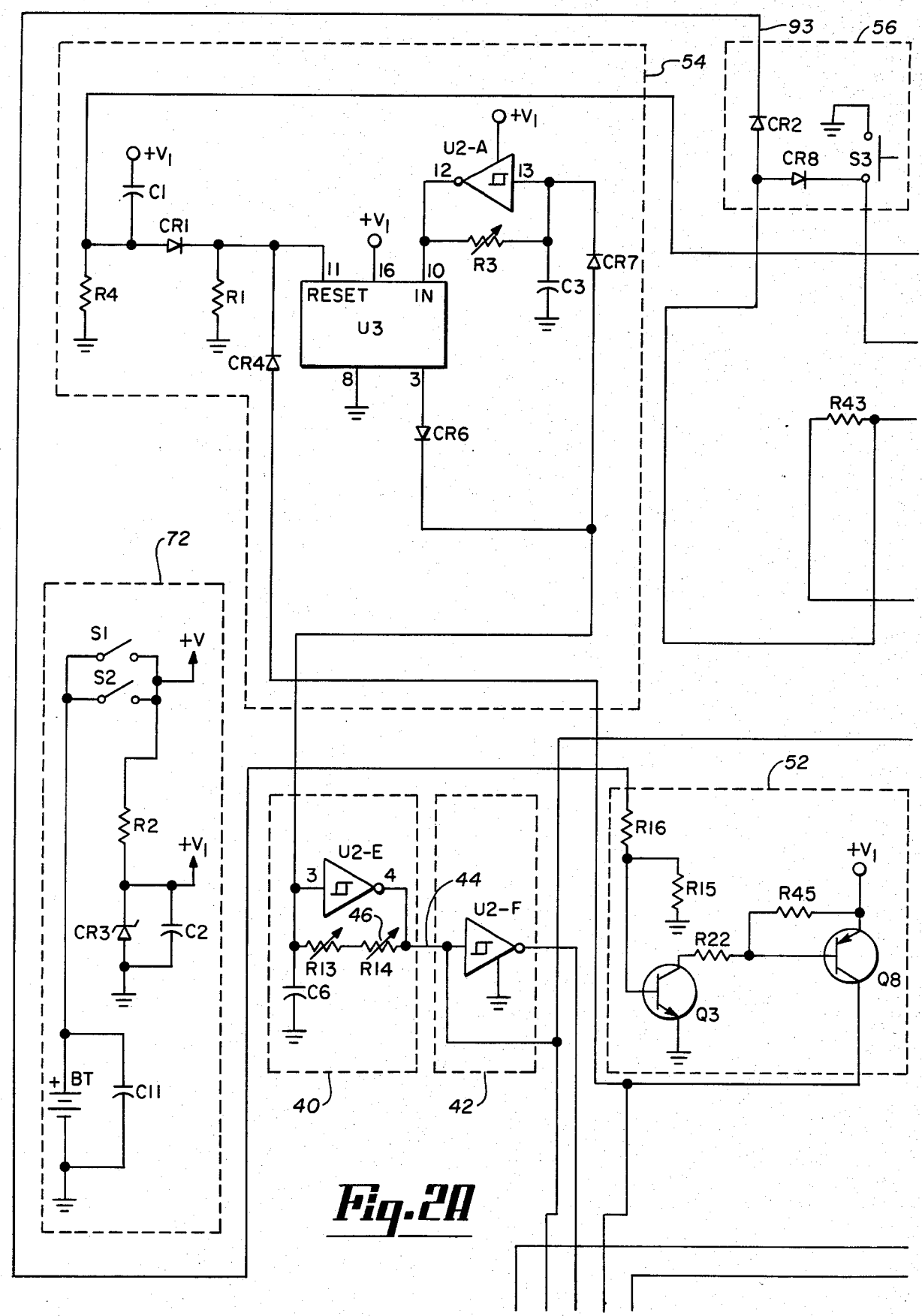
FIG. 2 is a layout of the schematics of FIGS. 2A through 2C which show the circuitry of the system of FIG. 1.

The overall structure of a dual channel neuromuscular stimulator system including a fail-safe system constructed according to the present invention is illustrated in the block diagram of FIG. 1. The embodiment illustrated is an ISOMOD ® stimulation system. The overall system 10 has a pair of output jacks 12 and 14 which can be connected to suitable stimulation electrodes in the case of an ESO (external) system or, in the case of an ESI implantable stimulation system, an RF transmitter.

Jacks 12 and 14 provide output from channels 1 and 2, respectively, of system 10. The circuitry of each channel is identical. Channels 1 and 2 have constant current (ESO) output circuits 16 and 18, respectively. Individual patient-adjusted amplitude controls 20 and 22 provide for adjustment of stimulation pulse amplitude from output circuits 16 and 18, respectively.

Drive signals 28 and 30 to the output circuits 16 and 18 are provided by identical channel 1 and channel 2 pulse width circuits 32 and 34. The pulse width circuits are driven by input signals 36 and 38 which are supplied respectively by a rate oscillator 40 and a phase inverter 42 which receives its input signal 44 from rate oscillator 40. Rate oscillator 40 has a physician controlled adjustment means 46 to alter the oscillation rate. In the preferred embodiment shown, the pulse rate is adjustable between 15 and 40 pulses per second.

Additional inputs to the pulse width circuits 32 and 34 are provided by pulse width ramp generation circuits 48 and 50, respectively. A fail-safe switching circuits 52 controls pulse width ramp generator circuits 48 and 50. Fail-safe switching circuit 52 also provides a switch logic signal as input to a fail-safe timer 54, which tests for the maximum stimulation time, according to the present invention. A momentary "on" switch 56 provides input to pulse width ramp generation circuits 48 and 50 through fail-safe switching circuit 52. Momentary "on" switch 56 is also referred to herein as a "constant stimulation" actuating switch.

An on/off cycler 62 provides cycler signal input to fail-safe switching circuit 52 for intermittent operation of the circuitry during treatment to apply pulses in bursts having a predetermined time duration and to suppress the pulse output during a predetermined "off" time or rest interval as established by physician actuated adjustment controls 66 and 68. On/off cycler 62 preferably allows alternative stimulation and resting intervals of 2 to 25 seconds each.

Figure 2B:
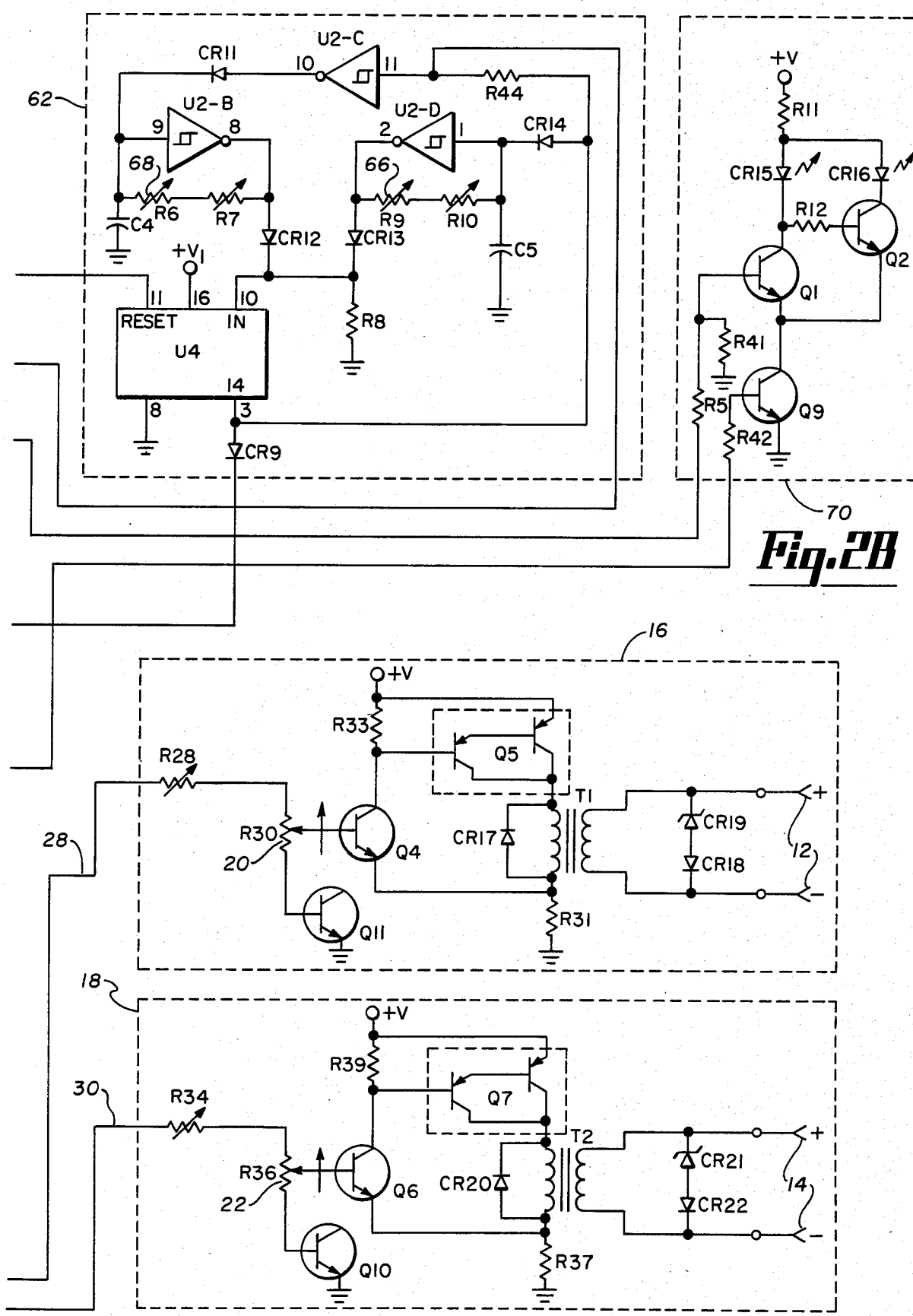
Figure 2C:
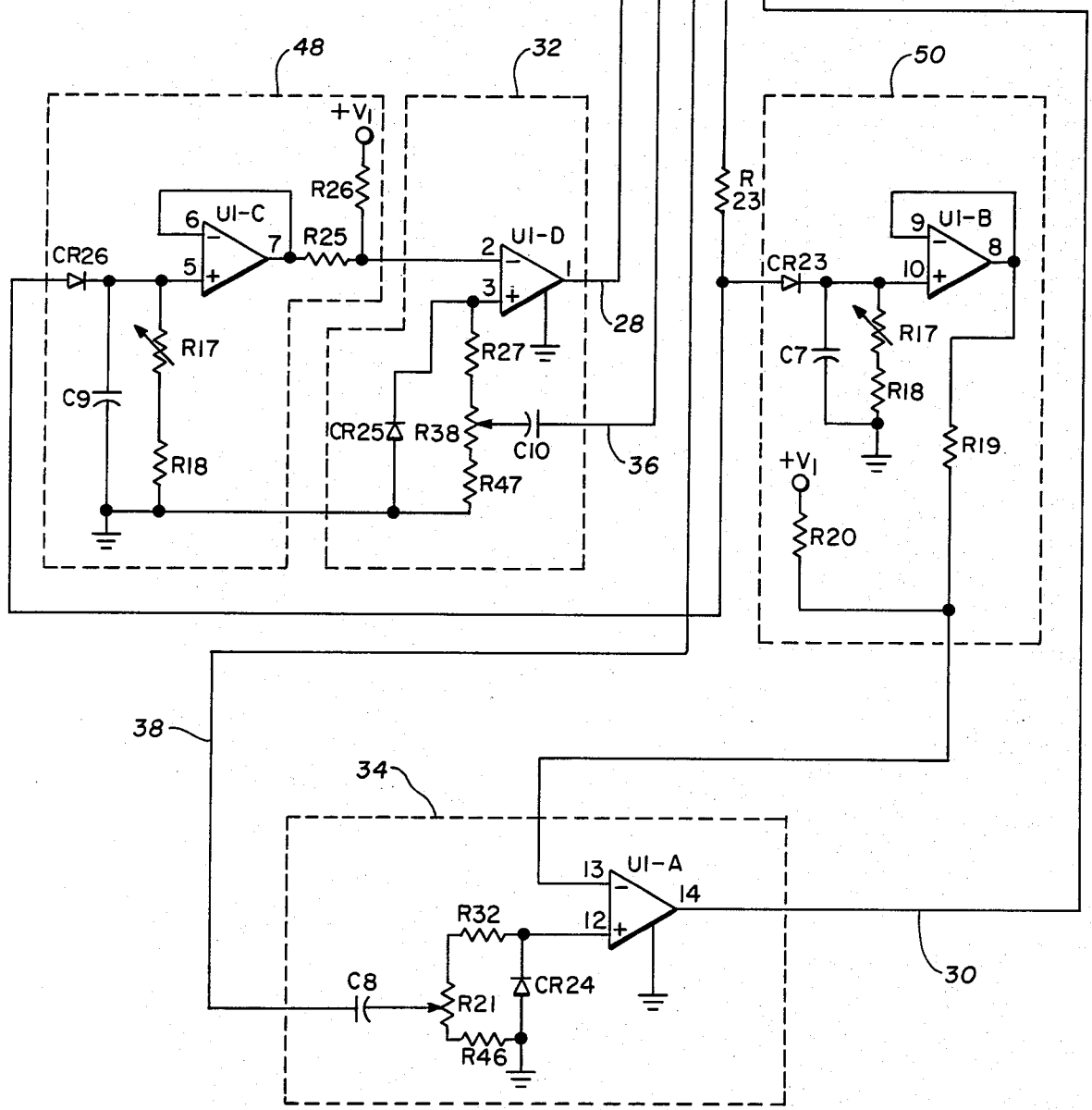

FIGS. 2A through 2C show a detailed schematic diagram of the dual channel neuromuscular stimulator system of FIG. 2 with a fail-safe device according to the present invention. The broken line boxes in FIGS. 2A through 2C correspond generally to the similarly numbered boxes in the functional block diagram of FIG. 1. Box 72 encloses power source circuitry not explicitly shown in FIG. 1.

The details of on/off cycler 62 are shown in FIG. 2B. The cycler 62 establishes the "on" or stimulation and "off" or resting time intervals which alternate during the selected treatment time in accordance with clinician adjustable controls 66 and 68 which are variable resistors appearing in the circuit of the cycler 62 as shown in FIG. 2B.

The variable resistor R9 or 66 is in the feedback circuit of Schmitt trigger U2D in series with a calibration resistor R10. In order to have Schmitt trigger U2D operate as an oscillator, a capacitor C5 is connected from its input terminal 1 to ground. The output of the Schmitt trigger oscillator U2D is passed through diode CR13 to terminal 10 which is the input to a 14-stage binary CMOS counter manufactured by Fairchild and others as Model 4020. Counter U4 is reset when a positive voltage is applied to reset terminal 11. A reset signal is provided by the capacitor C1 and resistor R4 voltage divider when the circuit is powered up. The output at the 14th stage of the binary counter U4 at pin 3 is connected through diode CR9 and is passed through resistor R43 to indicator circuit 70.

The "off" cycler is mechanized in FIG. 2B utilizing Schmitt trigger circuit U2B. The feedback resistors include a calibration resistor R7 and the physician controlled resistor R6 or 68. Capacitor C4 causes the circuit to oscillate in the same manner as the "on" cycler. The output signal of oscillator U2B at terminal 8 is connected through diode CR12 to the input to counter U4.

Oscillators U2B and U2D do not operate at the same time. The circuitry comprised of diode CR14, diode CR11 and Schmitt trigger U2C operates as a toggle to enable either oscillator U2B or U2D to oscillate at any one time. Schmitt trigger U2C is connected as an inverter between input terminal 9 of "off" oscillator U2B and input terminal 1 of "on" oscillator U2D. When the stimulation device is in the "on" cycle, pin 3 of counter U4 is at a low voltage so that the oscillator U2D is operating as the binary counter U4 counts until the output of binary stage 14 at pin 3 switches to a high voltage. When that voltage switches, it shuts down the stimulator by feeding the positive voltage through diode CR9, resistor R43 and diode CR2 to switching circuit S2. The high voltage at pin 3 of counters U4 feeds through diode CR14 to stop the operation of oscillator U2D. That high voltage is also conducted through resistor R44 to U2C which inverts it to remove the high logic signal that was conducted through CR11 to keep oscillator U2B stopped. Thus, U2B starts to operate when U2D is shut down. By adjustment of the operating frequencies of U2D and U2B, the "on" and "off" times of the preferred embodiment shown can be adjusted over the range of 2 to 25 seconds.

The constant stimulation momentary on switch (block 56) has a switch designated S3 in FIG. 2A. When switch S3 is actuated, it connects the cathode of diode CR8 to ground. This inhibits signals coming from counter U4 so that cycler 62 is inhibited from shutting the circuit off during the time that the momentary contact switch S3 is closed.

The closure of switch S3 also applies a ground to the input of Schmitt trigger U2C which puts a high logic signal on the output of Schmitt trigger U2C to stop oscillator U2B. This operational feature allows oscillator U2D to keep running until counter U4 reaches the end of its time cycle so that when the pressure on the constant stimulation switch S3 is removed, the cycler 62 is in the "off" position and at the beginning of the "off" cycle. This is an important operational feature because after continued stimulation under control of the constant stimulation switch has been applied to a muscle group, it is extremely desirable to allow the muscle to recover in a nonstimulated condition. Allowing the "on" cycler to continue to run to bring the circuit back into the beginning of the "off" cycle during the time that constant stimulation is applied accomplishes this desirable objective in the preferred embodiment of the stimulator shown.

The output signal at terminal 3 of counter U4 is connected through resistor R43 to the cycler indicator lights 70. The signal passes through resistor R5 to the base of NPN transistor Q1 which has its base connected to ground through resistor R41. The collector of transistor Q1 is connected to the base of transistor Q2 through resistor R12. A green light emitting diode (LED) CR15 is connected to the collector of transistor Q1 while a red LED CR16 is connected to the collector of transistor Q2. The anodes of LEDs CR15 and CR16 are connected through a current limiting resistor R11 to the unregulated supply voltage +V. The emitters of transistors Q1 and Q2 are tied together and connected to the collector of NPN transistor Q9 which receives an input signal through resistor R42. Either transistor Q1 or Q2 is turned on, depending upon whether the output of counter U4 is in a high or low condition. Transistor Q9 is turned on for each half cycle of the output of rate oscillator 40. The LEDs thus operate to indicate whether the stimulation is "on" or "off". During the "on" cycle or when switch S3 is pushed for constant stimulation, the red light of LED CR16 will come on. During the "off" cycle or once the treatment timer shuts the device down, the green light of LED CR15 comes on. Since transistor Q9 is turned on and off at the rate of the rate oscillator, the light emitting diodes CR15 and CR16 are blinked at a rate corresponding to the rate of the oscillator and the power consumption to drive the indicators is substantially reduced. If the rate of oscillator 40 is set at a very low rate, the blinking is visible to the user's eye.

The signal from the output of timer U4 is conducted through resistor R43, CR2, conductor 93 and resistor R16 to the base of NPN transistor Q3. The base of transistor Q3 is connected to ground through resistor R15. The collector of transistor Q3 is connected through resistor R22 to the base of transistor Q8. The emitter of NPN transistor Q8 is connected to the regulated supply +V1. The base of transistor Q8 is connected to the regulated supply +V1 through resistor R45 and the collector of transistor Q8 is connected through resistor R23 to diodes CR26 and CR23 at the inputs of identical channel 1 and channel 2 ramp circuits 48 and 50, respectively, as shown in FIG. 2C. The detailed circuitry of pulse width circuits 32 and 34 are also identical. Accordingly, it is necessary only to describe the operation of the channel 1 output circuitry since the channel 2 output circuitry is essentially identical.

When the counter U4 switches to a positive signal, that signal charges capacitor C9 of ramp circuit 48 rapidly through resistor R23 which has a low impedance. Operational amplifiers U1A, U1B, U1C, and U1D are part of a quad package such as a National Semiconductor Model LM224. The positive voltage applied at noninverting input terminal 5 of operational amplifier U1C produces a positive voltage at the output terminal 7 of operational amplifier U1C which is connected through resistor R25 to the noninverting input of operational amplifier U1D in the channel 1 pulse width circuit 32 which, as described below, turns off the channel 1 output. When the positive signal holding channel 1 off is removed from the anode of diode CR26, capacitor C9, which had been previously charged to a high logic signal, begins to discharge through the series combination of adjustable resistor R17 and fixed resistor R18.

Since operational amplifier U1C is connected as a voltage follower, the positive output of operational amplifier U1C gradually diminishes. The diminishing ramp signal from the output of ramp circuit 48 is summed in the pulse width circuit 32 with a square wave rate signal on conductor 36 produced by rate oscillator 40, the operation of which is discussed below.

The square wave rate signal on conductor 36 is passed through capacitor C10 to the wiper of variable resistor R38 and through resistor R27 to the noninverting input terminal 3 of operational amplifier U1D. A diode CR25 has its anode connected to ground and its cathode connected to pin 3 of operational amplifier U1D. The values of resistor R38, resistor 47 and capacitor C10 are selected to give a time constant which, when applied to the square wave signal at the output of oscillator 40, produces a nominal 225 microsecond pulse width for the output pulses. The pulse width of the drive signal on conductor 28 is inversely dependent upon the magnitude of the ramp input to operational amplifier U1D produced by the ramp circuit 48. As the output of operational amplifier U1C follows capacitor C9 to zero, +V1 divides across resistors R26 and R25 to ground through operational amplifier U1C to provide a fixed bias to pin 2 of operational amplifier U1D.

The signal on conductor 28 is connected to the output circuit 16 of channel 1. The signal is an increasing pulse width signal beginning from a very narrow signal when the positive voltage is removed from the anode of diode CR26 and increasing to the full nominal pulse width after the ramp signal at the output of the ramp circuit 48 decreases to zero. As the output of operational amplifier U1C follows capacitor C9 to zero, +V1 divides across resistors R26 and R25 to ground through operational amplifier U1C to provide a fixed bias to pin 2 of operational amplifier U1D. The leading edge of the pulse occurs at intervals determined by the square wave signal produced by oscillator 40 so the leading edges of the drive pulses on conductor 28 occur at a fixed pulse rate.

Rate oscillator 40 is based on Schmitt trigger U2E and its adjustable feedback resistors R13 and 46 and timing capacitor C6. The drive signal to channel 1 is inverted by Schmitt trigger U2F so that the identical drive circuitry of channels 1 and 2 is not in the "on" condition at the same time. This is necessary to avoid undesirable overloading of the power supply. Cells BT1, BT2 and BT3 in power source circuitry 72 provide the power for the device. Capacitors C11 and C12 are large capacitors used to facilitate driving the output current. They are back-to-back to prevent damage due to improperly installed batteries.

Because the output circuits 16 and 18 are identical, only the channel 1 output circuit 16 is described in detail. The drive signal on conductor 28 is passed through a variable calibration resistor R28. The drive signal for transistor Q4 is taken from the wiper of the patient adjustment amplitude control or resistor 20. The winding of potentiometer or a variable resistor 20 is connected to the base of a grounded emitter open collector NPN transistor Q11 to provide temperature and base-emitter voltage compensation for transistor Q4. The collector of transistor Q4 is connected to the base of PNP Darlington transistor pair Q5 which has its emitter connected to the +V supply. The Darlington base junction is also connected to the positive supply through resistor R33. The collector of transistor Q5 is connected through the primary winding of isolation transformer T1 and a current measuring resistor R31 to ground. Resistor R31 has an extremely low resistance and serves as a current sensor to force transistor Q5 to drive a constant current in the primary of transformer T1.

The current feedback is obtained as follows. The base-emitter voltage of transistors Q4 and Q11 are matched so that the voltage from conrol 20 or variable resistor R30 is applied to resistor R31 to drive a current therein proportional to the setting of control 20. Thus, the transformer T1 primary current is fixed as a selected current. Current transformer T1 produces a constant current output for a load impedance from 100 to 1,000 ohms.

A flyback diode CR17 suppresses the inductive surge voltage across the primary winding of transformer T1 when Q5 shuts off at the completion of a pulse.

The secondary winding of transformer T1 is connected to output terminals 12. Zener diode CR19 is a safety diode to prevent the voltage across output terminals 12 rising to an excessive value if the output impedance across terminals 12 is extremely high due to a loose electrode or some similar kind of open circuit condition. Diode CR18 is used to keep CR19 from forward conducting the negative or biphasic portion of the pulse, thus maintaining a zero net DC output to the patient. The transformer produces a balanced, biphasic, rectangular, asymmetric waveform with a zero net DC component.

The fail-safe timer 54 illustrated utilizes as the timing means a 14-stage binary CMOS counter U3 which is, like counter U4, manufactured by Fairchild and others as model 4020. The numbers at the outside of the box of counter U3 denote the manufacturer's pin designations for the various terminals of counter U3. The output from the counter U3 at pin 3 is from the 14th counter stage. Input to counter U3 at terminal 10 is provided by a Schmitt trigger circuit U2A utilizing one element of a Schmitt trigger module such as model 40106 unit manufactured by RCA, National Semiconductor and others which contains six Schmitt triggers (U2A-U2F). The adjustable feedback resistor R3 and timing capacitor C3 operate to establish the frequency of Schmitt trigger U2A as an oscillator to provide a clock signal to the input to counter U3. In a preferred embodiment of the stimulator, the clock signal is selected to provide output at terminal 14 of the binary counter U3 at 40 seconds.

The counter U3 is reset as the unit is initially powered up by the voltage divider comprised of capacitor C1, diode CR1 and resistor R1. When the "power on" switches S1 and/or S2 are closed, the +V voltage is applied to the various circuits to which it is connected and a regulated voltage V1 is developed across diode CR3. In the preferred embodiment shown, switches S1 and S2 are included in the patient amplitude controls 20 and 22, respectively. Capacitor C2 is charged almost instantaneously through limiting resistor R2 and provides a filtering effect for the regulated voltage V1 across diode CR3. When V1 is applied to capacitor C1 as either switch S1 or S2 is closed to energize the stimulator, capacitor C1 begins with no stored voltage so that the charging current passing from V1 to ground through diode CR1 and resistor R1 develops a positive voltage across resistor R1 to apply a reset signal to terminal 11 of counter U3. After capacitor C1 is fully charged, the charging current drops to zero and thereby removes the reset signal to allow the input clock signal at terminal 10 of counter U3 to begin the counting operation.

Counter U3 times the "on" interval of stimulation. When $2^{13}$ pulses are provided from the oscillator including Schmitt trigger U2A, output pin 3 of counter U3 goes high. The signal from pin 3 is provided through diodes CR6 and CR7 to Schmitt trigger U2A to shut off the oscillator. This prevents pin 3 of counter U3 from switching low again after another $2^{13}$ pulses.

The signal from pin 3 of counter U3 is applied through diodes CR6 and CR10 to pin 3 of Schmitt trigger U2E in rate oscillator 40. The signal of pin 3 of Schmitt trigger U2E stops rate oscillator 40, thus preventing stimulator output signals. Schmitt trigger U2E is held in a low output state which turns off transistor Q9, thereby turning off LEDs CR16 and CR15 of indicator lights 70.

As the stimulator 10 cycles normally, in the mode where the "on" time is less than the timeout period of counter U3 ($<2^{13}$ pulses from the oscillator employing Schimtt trigger U2A), transistor Q8 of fail-safe switching circuit 52 turns on and off inversely with the on and off cycle of the cycler 62. Each time stimulator 10 cycles off, transistor Q8 turns on and resets counter U3 by providing a signal to pin 11 through diode CR4. If cycler 62 or any associated circuitry malfunctions, transistor Q8 will not turn on to reset pin 3 of counter U3. In this case counter U3 will time out when pin 3 goes high. This shuts off all stimulator output and the indicator lights 70. Similarly, if the constant stimulation switch S2 is depressed for a time exceeding the timeout period of counter U3, transistor Q8 does not turn on to reset counter U3. Output from pin 3 of counter U3 is then provided to Schmitt trigger U2E to shut off stimulator output.

When the constant stimulation switch S2 is released or any malfunctioning circuitry heals, counter U3 receives a reset pulse at pin 11 the next time output pin 3 of counter U4 switches high. This pulse is transmitted through transistor Q3, transistor Q8, and diode CR4 to pin 11 of counter U3. Diode CR1 prevents such pulses from transistor Q8 from resetting counter U4, yet enabling both counters U4 and U3 to be reset upon powerup by the single capacitor C1.

Therefore, the length of the "on" interval from cycler 62 is constantly monitored by fail-safe timer 54. Each time the "on" time interval ends, fail-safe switching circuit 52 resets fail-safe timer 54. Should the "on" interval exceed the timeout interval of fail-safe timer 54, rate oscillator 40 will be inhibited from producing output. Therefore, in the unlikely occurrence of circuitry malfunction, the stimulator will not continue to produce output.

Should a user of stimulator 10 misjudge the amount of time he depresses the momentary "on" switch 56, fail-safe switching circuitry 52 will not reset fail-safe timer 54. Fail-safe timer 54 will then time out and inhibit output rate oscillator 40, preventing excess stimulation.

The fail-safe system of the present invention prevents extended periods of stimulation which can result in back soreness in patients who are using muscle stimulator 10 for extended periods of time, such as scoliosis patients who receive stimulation through the entire night. Although this invention has been described with reference to a particular embodiment, one skilled in the art can apply the present invention to various circuits and embodiments to achieve its intended purpose.

What is claimed is:

1. In a tissue stimulator having cycler means for producing a periodic stimulation signal with a predetermined "on" time interval repetitively alternating with a predetermined "off" time interval, the improvement comprising:
    timer means for timing the duration of the "on" time interval;
    time out means in the timer means for shutting off the stimulation signal when a maximum time interval is reached before the termination of the "on" time interval;
    momentary contact switch means for producing a constant stimulation signal when the momentary switch means is actuated;
    override means in the cycler means for generating the "on" interval during actuation of the momentary contact switch means; and
    wherein the time out means turns off the timer means if the "on" interval initiated by the momentary contact switch means exceeds the predetermined maximum interval.

2. A fail-safe tissue stimulator comprising:
    oscillator means for producing a periodic signal at a predetermined repetition rate;
    rate control means coupled to the oscillator means for altering the repetition rate of the oscillator means, the rate control means including means for deactivating the rate control means in response to a time out signal;
    cycler means for repetitively producing a cycler logic signal which remains at a first level for a predetermined "on" time interval and a second level for a predetermined "off" time interval;
    first cycler control means coupled to the cycler means for setting the predetermined "on" time interval;
    second cycler control means coupled to the cycler means for setting the predetermined "off" time interval;
    fail-safe switch means for receiving the cycler logic signal and for generating a switch logic signal;

ramp generator circuit means for receiving the switch logic signal and for producing an output ramp signal changing from a first ramp level of a second ramp level at the predetermined rate as a function of the receipt of a ramp control signal;

ramp generator control means coupled to the ramp generator circuit means for providing the ramp control signal;

pulse width circuit means coupled to receive the ramp signal from the ramp generator circuit means and to receive the output signal from the oscillator means and for producing a pulse signal having a pulse width depending upon the output ramp signal from the ramp generator circuit means and the predetermined repetition rate of the oscillator means;

output circuit means connected to receive the pulse signal of the pulse width circuit means and for producing an output signal;

timer means for timing the length of each "on" time interval of the cycler means;

time out means for turning off the timer means and providing the time out signal to turn off the rate oscillator means if the "on" interval exceeds a predetermined maximum interval;

momentary contact switch means for producing a constant stimulation signal when the momentary switch means is actuated;

override means in the cycler means for generating the "on" interval during actuation of the momentary contact switch means; and wherein the time out means turns off the timer means if the "on" interval initiated by the momentary contact switch means exceeds the predetermined maximum interval.

* * * * *